United States Patent [19]
Ishii et al.

[11] Patent Number: 4,712,428
[45] Date of Patent: Dec. 15, 1987

[54] ULTRASONIC FLAW DETECTOR PROBE

[75] Inventors: Yugoro Ishii, Hino; Motohisa Onozawa, Sugakawa; Akihiko Katamine, Yokohama, all of Japan

[73] Assignee: Kabushiki Kaisha Komatsu Seisakusho, Tokyo, Japan

[21] Appl. No.: 887,247

[22] Filed: Jul. 21, 1986

[51] Int. Cl.$^4$ ............................................. G01N 29/04
[52] U.S. Cl. ..................................................... 73/644
[58] Field of Search ................ 73/649, 644, 642, 627, 73/629; 310/335

[56] References Cited
U.S. PATENT DOCUMENTS 3,895,685  7/1975  Gillette et al. ................. 73/627 X
4,398,421  8/1983  White ............................. 73/644 X

FOREIGN PATENT DOCUMENTS 52-45388  4/1977  Japan .
52-87081  7/1977  Japan .

Primary Examiner—Jerry W. Myracle
Attorney, Agent, or Firm—Frost & Jacobs

[57] ABSTRACT

A first ultrasonic transducer (e.g. for wave reception) is mounted at the open bottom of a probe housing. One or more lenses are disposed around the first transducer and have a sloping surface or surfaces on which at least two second ultrasonic transducers (e.g. for transmission) are mounted. The second ultrasonic transducers provide paths of ultrasonic wave propagation extending through the lens or lenses and crossing each other at a point just below the first transducer. In an alternate embodiment the first transducer is made adjustably movable up and down relative to the lens or lenses, and an elastic coupling is provided through which the first transducer is held against an irregularly shaped object to be inspected.

12 Claims, 15 Drawing Figures

ULTRASONIC FLAW DETECTOR PROBE

BACKGROUND OF THE INVENTION

Our invention pertains to a probe for use in ultrasonically detecting flaws in objects such as castings and welds.

Ultrasonic flaw detection systems have found a widespread acceptance in various industries as a versatile, efficient tool for the detection of internal cracks, cavities, etc., in a variety of solid objects. They commonly include a probe to be held against the object. The probe comprises ultrasonic transducers for the transmission and reception of ultrasonic vibrations, arranged to determine the distance to a wave reflecting internal flaw in the object. High frequency electrical oscillations are transferred into mechanical vibrations which are sent out into the object. Any transmitted or reflected mechanical vibrations are received by the same probe, transferred back to electrical oscillations, and fed back through an amplifier for evaluation through display on a cathode ray tube. Japanese Laid Open Patent Applications Nos. 52-45388 and 52-87081 disclose examples of such ultrasonic probes.

Most of these and other known ultrasonic probes have had intrinsic "insensitive zones", where small flaws are not clearly detectable, immediately below the surface of the object being tested. We have found that such insensitive zones are attributable to the undue divergence of the ultrasonic beam generated by the prior art devices.

Another weakness of the known ultrasonic probes is that their performance is easy to be adversely affected by the irregular shape or roughness of the surface of the object under inspection. For this reason they have not necessarily been capable of detecting small flaws when held directly against weld beads or "black skins" of iron castings.

As an additional drawback, the known devices have mostly been capable of detecting flaws only in a limited region under the probe. Unnecessarily long time has had to be expended for inspecting greater regions.

SUMMARY OF THE INVENTION

We have hereby invented how to design an ultrasonic probe so as to make it free from any insensitive zone and to enhance its sensitivity to small flaws regardless of the surface conditions of the object being tested.

According to our invention, stated in brief, a probe for ultrasonic flaw detection is provided which comprises an open bottom housing having an axis passing therethrough. A first ultrasonic transducer is disposed at the open bottom of the housing and is centered about the axis thereof. Also disposed within the housing, lens means is exposed through its open bottom and has at least one sloping surface at an angle to the axis of the housing. At least one pair of second ultrasonic transducers are mounted on the sloping surface of the lens so as to provide paths of ultrasonic vibrations extending through the lens means, the paths of ultrasonic crossing each other at that point on the axis of the housing which is located outside the open bottom thereof.

The first and the second transducers may be reversibly employed for transmission or reception of ultrasonic waves. In preferred embodiments disclosed herein, the first transducer is used for reception, and the second transducers for transmission. The beams of mechanical vibrations emitted by the second transducers at an ultrasonic frequency meet each other just below the first transducer. The meeting beams are effective to amplify the reflection from a flaw existing in the neighborhood of the meeting point, the amplified reflection being received by the first transducer disposed centrally at the bottom of the probe housing. Thus the probe of our invention can detect smaller flaws than heretofore.

As is evident from the foregoing principles of our invention, flaws lying at any depth of the object are detectable merely by changing the angle of the sloping surface of the lens means, on which the second transducers are mounted, with respect to the probe axis. It will also be appreciated that the probe of our invention is unaffected by the surface conditions of the object under inspection and so can operate properly even when held against, for example, the blackened surface layers of iron castings or against weld lines. Experiment has also proved that the probe of our invention has no insensitive zone, being highly sensitive to flaws just under the surface of the object.

In an additional embodiment of our invention, the first ultrasonic transducer is made adjustably movable back and forth relative to the housing in the direction of the probe axis, as required by the surface configuration of the object or by the depth of the object to be investigated. The movable transducer is further provided with an elastic coupling through which the probe can make close contact with objects of any surface shape such as weld beads. The movable first transducer in conjunction with the elastic coupling materially enhances the sensitivity, versatility and efficiency of the probe with respect to a wide variety of objects to be tested.

The above and other features and advantages of our invention and the manner of realizing them will become more apparent, and the invention itself will best be understood, from a study of the following description and appended claims, with reference had to the attached drawings showing some preferred embodiments of our invention.

DESCRIPTION OF THE PREFERRED EMBODIMENTS

Figure 1:
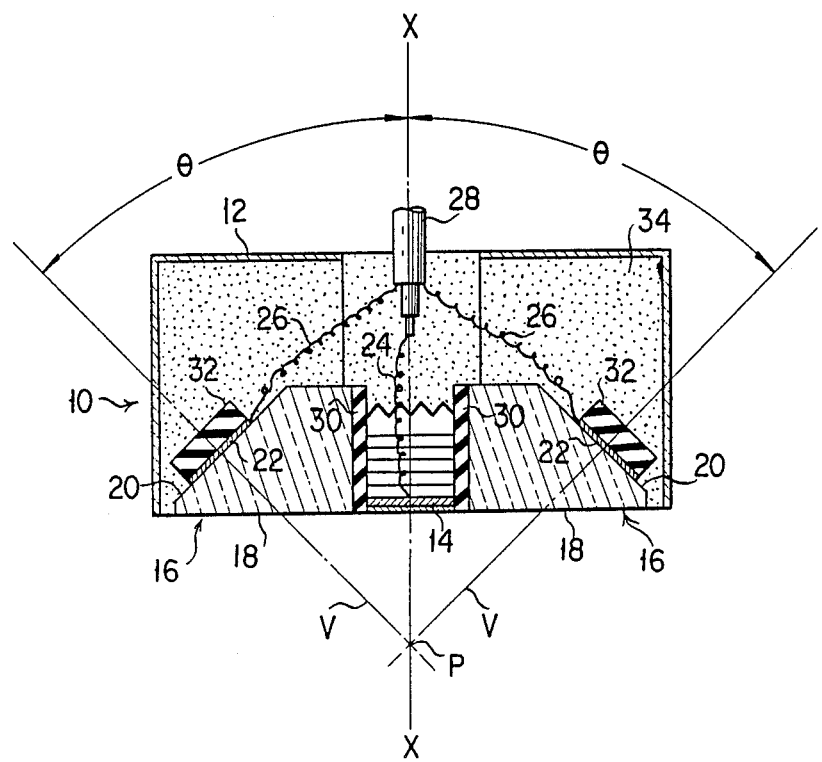
FIG. 1 is an axial section through a preferred form of the ultrasonic flaw detecting probe constructed in accordance with the novel concepts of our invention.

We will now describe in detail the ultrasonic probe of our invention in terms of its first preferred form in FIG. 1. Generally designated 10, the representative probe has an open bottom housing 12 having mounted at its open bottom a first ultrasonic transducer 14 which is used in this embodiment for the reception of ultrasonic vibrations and the conversion of the received vibrations into electric oscillations. The first ultrasonic transducer 14 is centered about an axis X—X extending vertically through the geometrical center of the probe 10.

Figure 2:
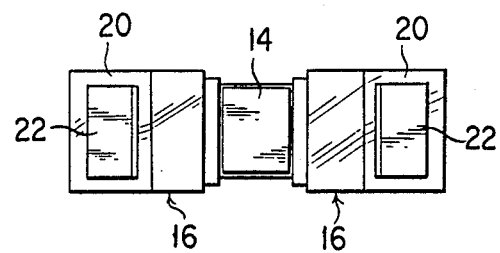
FIG. 2 is a plan view of the ultrasonic transducers and lenses of the probe of FIG. 1.

As will be seen also from FIG. 2, a pair of lenses 16 of acrylic resin, aluminum or like material are disposed on the opposite sides of the first ultrasonic transducer 14 and within the probe housing 12. Exposed through the open bottom of the probe housing 12, the bottoms 18 of the lenses 16 are herein shown flattened for direct contact with flat surfaced objects to be tested. Each lens 16 is chamfered at 20 to provide a surface sloping downwardly as it extends away from the probe axis X—X.

A pair of second ultrasonic transducers 22, herein used for the transmission of ultrasonic vibrations in beam form, are mounted one on the sloping surface 20 of each lens 16. The sloping surfaces 20 of both lenses 16 are at the same angle to, and of bilateral symmetry about, the probe axis X—X, so that the paths V of ultrasonic vibrations due to the second ultrasonic transducers 22 are at the same angle $\theta$ to the probe axis. Thus, passing through the respective lenses 16, the two paths V of ultrasonic vibrations cross each other at the point P on the probe axis X—X located under the first ultrasonic transducer 14.

The first 14 and second 22 ultrasonic transducers are electrically connected to leads 24 and 26, respectively. Joined into a common cable 28, these leads are coupled to the associated main instrument, not shown, of the flaw detection system which may include a cathode ray tube for visual presentation of waveforms.

The probe 10 of our invention further features provisions for acoustically insulating the first 14 and second 22 ultrasonic transducers from each other. Such provisions incude vibration dampers 30 of polyurethane rubber or like material mounted between first ultrasonic transducer 14 and lenses 16, similar dampers 32 attached to the second ultrasonic transducers 22, and a body 34 of suitable damping material filled in the probe housing 12.

Figure 3:
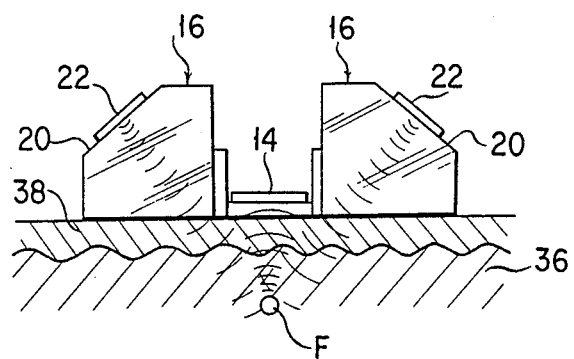
FIG. 3 is a diagrammatic side elevation of the ultrasonic transducers and lenses of the FIG. 1 probe, shown together with an object being tested in order to illustrate its mode of operation.

The operation of the probe 10 will be best understood from a consideration of FIG. 3, in which we have shown the probe placed against an iron casting 36, having a "black skin" 38, as an example of object to be inspected by the device. An electric signal of an ultrasonic frequency (e.g. 5 MHz) may be impressed to the second ultrasonic transducers 22 thereby causing the same to generate mechanical vibrations at the same frequency. Propagating through the lenses 16, the two beams of ultrasonic vibrations will meet each other at the point P on the probe axis X—X, which point in this case is under the "black skin" 38. If a flaw F exists in the neighborhood of the point P, the first ultrasonic transducer 14 will receive the vibrations reflected therefrom and translate them into electrical oscillations for delivery to the unshown main instrument.

Figure 4:
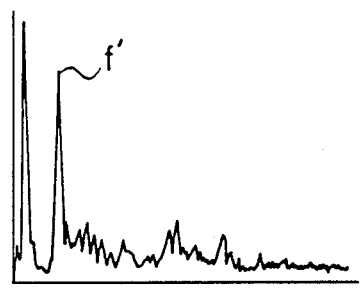
FIG. 4 is a diagram of a waveform as exhibited by a flaw detector incorporating the FIG. 1 probe on testing an iron casting.

FIG. 4 is an example of waveform displayed by the main instrument in response to the signal sent back from the probe 10 as in the foregoing. The peak amplitude f of the displayed waveform indicates the flaw F, which may be construed by skilled operators as a pinhole with a diameter of 1 mm or so.

Figure 5:
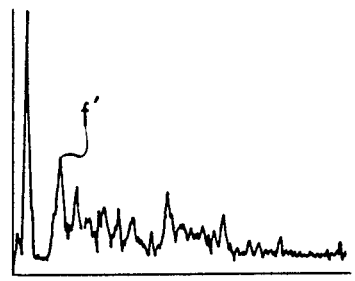
FIG. 5 is a diagram showing another example of waveform displayed by the flaw detector incorporating the FIG. 1 probe.

Articles of materials such as cast iron, copper or clad metal have been known, because of the presence of coarse particles or carbon, to attenuate ultrasonic vibrations to such an extent that a majority of the prior art probes with their insensitive zones have been hardly capable of detecting minute flaws lying immediately below the surface. We have overcome this difficulty by causing the beams of ultrasonic vibrations from the separate transmitting transducers 22 to meet each other just under the receiving transducer 14. So united, the ultrasonic vibrations amplify themselves, and the amplified vibrations are reflected by the flaw F for reception by the first transducer 14. As demonstrated by another example of waveform given in FIG. 5, which was obtained by use of the probe 10 of our invention, a pinhole as small in diameter as 0.5 mm is detectable from the peak f'. The waveforms of FIGS. 4 and 5 further indicate that the probe of our invention has no insensitive zone, the waveforms being free from noise component before the echoes from the flaws.

The insensitive zones of ultrasonic probes in general are due in part to the multiple reflections of the ultrasonic waves within the lenses. In most cases the insensitive zones may be from 4 to 5 mm from the surface of the object. We have acoustically isolated the ultrasonic transducers 14 and 22 from each other by the damping means 30, 32 and 34 for the elimination of an insensitive zone.

Figure 6A:
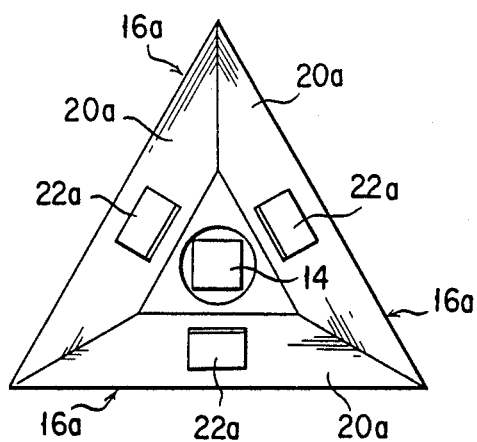
FIG. 6A is a plan view of another example of arrangement of lens means and second ultrasonic transducers in accordance with our invention.
Figure 6B:
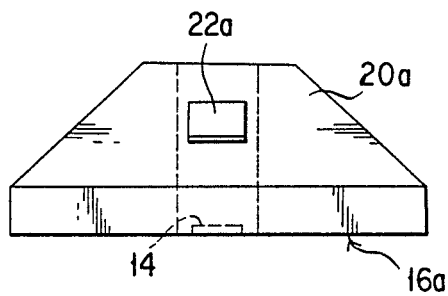
FIG. 6B is a side elevation of the arrangement of FIG. 6A.

The arrangement of the lenses 16 and second ultrasonic transducers 22 thereon in the FIG. 1 embodiment is by way of example only and is subject to a variety of modifications within the broad teaching hereof. Thus, in FIGS. 6A and 6B, we have employed three lenses 16a around the first ultrasonic transducer 14. Each lens 16a has a sloping surface 20a on which one second ultrasonic transducer 22a is mounted. Of course, we could employ a greater number of lenses, and as many second ultrasonic transducers, of similar arrangement.

Figure 7A:
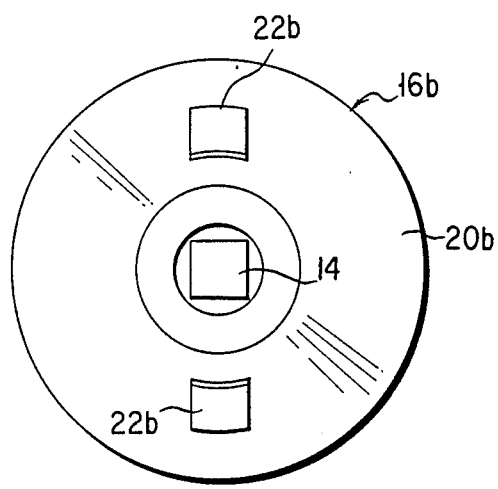
FIG. 7A is a plan view of yet another example of arrangement of lens means and second ultrasonic transducers in accordance with our invention.
Figure 7B:
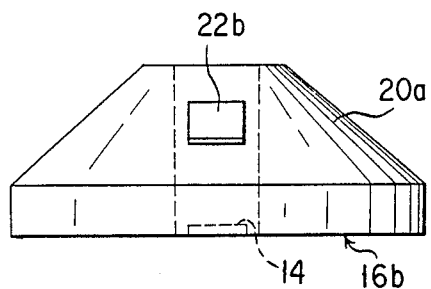
FIG. 7B is a side elevation of the arrangement of FIG. 7A.

Another modification shown in FIGS. 7A and 7B has but one lens 16b substantially in the shape of a truncated cone. At least two second ultrasonic transducers 22b may be mounted on the sloping surface 20b of this lens 16a.

Figure 8A:
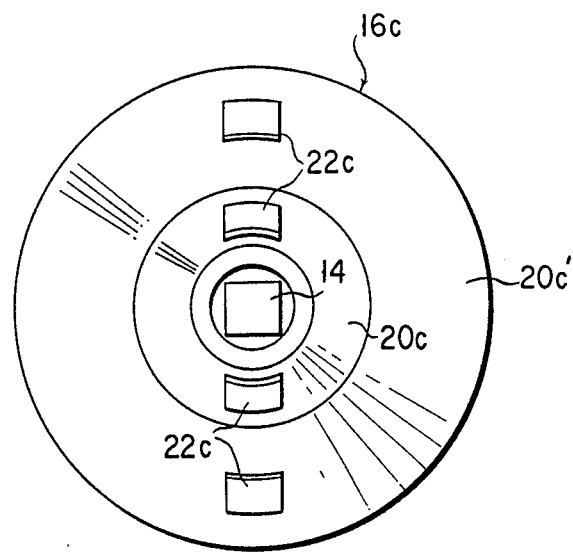
FIG. 8A is a plan view of a further example of arrangement of lens means and second ultrasonic transducers in accordance with our invention.
Figure 8B:
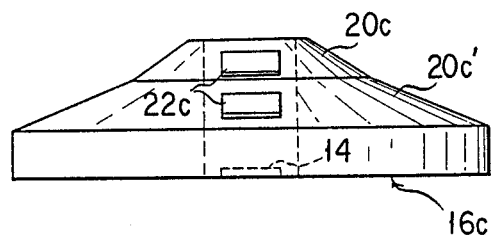
FIG. 8B is a side elevation of the arrangement of FIG. 8A.

In a further modification illustrated in FIGS. 8A and 8B, we have employed a single lens 16c whose shape might be described as a stack of two truncated cones concentric about the probe axis. The two cones have sloping surfaces 20c and 20c' of different angles on which two second ultrasonic transducers 22c are mounted.

Figure 9:
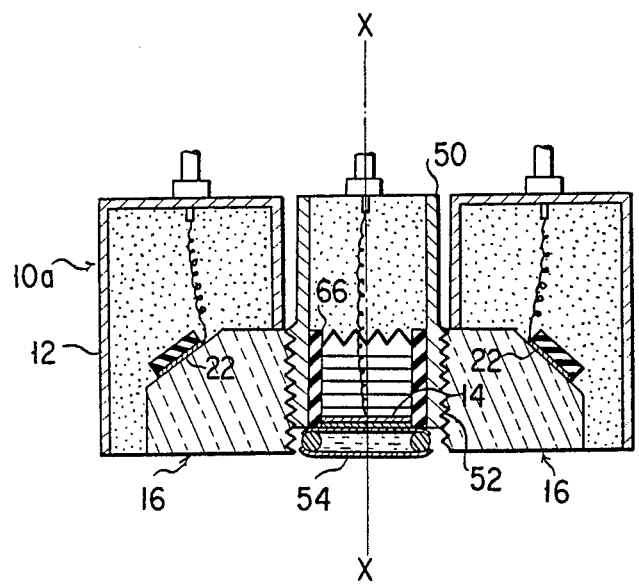
FIG. 9 is an axial section through an alternative form of the flaw detecting probe in accordance with our invention.

FIG. 9 shows an ultrasonic probe 10a of alternative construction in accordance with our invention. The alternative probe 10a features a movable transducer holder 50 carrying the first ultrasonic transducer 3 for adjustably varying its vertical position with respect to the pair of lenses 16. In the shape of a hollow cylinder, the transducer holder 50 is centered about the probe axis X—X and is threadedly engaged at 52 with the lenses 16. Thus, on being revolved bidirectionally relative to the probe housing 12, the transducer holder 50 is movable up and down along the probe axis X—X with respect to the lenses 16. Mounted to this holder 50 in a manner to be detailed subsequently, the first ultrasonic transducer 14 travels therewith to a required position with respect to the lenses 16.

Figure 10:
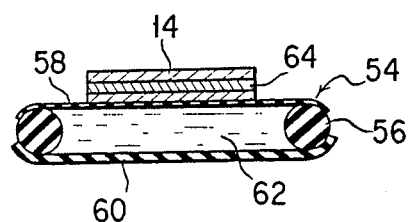
FIG. 10 is is an enlarged section through the elastic coupling of the probe of FIG. 9.

Another feature of the alternative probe 10a resides in an elastic coupling 54 through which the first ultrasonic transducer 14 is to be held against a desired object for more accurate flaw detection. As illustrated on an enlarged scale in FIG. 10, the elastic coupling 54 includes a ring 56 of rigid material disposed concentrically under the transducer holder 50 and having an outside diameter approximately equal to, or slightly less than, the inside diameter of the transducer holder. Two sheets 58 and 60 of elastic material such as crude rubber are attached to the top and bottom sides of the ring 56, defining in combination a fluid chamber 62 filled with a fluid such as low viscosity oil. The upper elastic sheet 58 is thinner than the lower elastic sheet 60 and has the first ultrasonic transducer 14 bonded centrally thereon via a quarter wave plate 64.

The desired fluid may be filled in the fluid chamber 62 by the familiar injector through the lower elastic sheet 60. The hole created by the injector will serve to permit the fluid to ooze out through the lower elastic sheet 60 when the elastic coupling 54 is held against an object.

The elastic coupling 54 of the foregoing construction is mounted to the bottom end of the transducer holder 50 via a damper 66. Accordingly, the elastic coupling 54 with the first ultrasonic transducer 14 thereon is movable up and down with the transducer holder 50.

The alternative probe 10a is analogous in the other details of construction with the probe 10 of FIG. 1. However, in this probe 10a, we recommend that the first ultrasonic transducer 14 be used for transmission, and the second ultrasonic transducers 22 for reception, although they might be used for the opposite purposes as in the foregoing embodiment.

Figure 11:
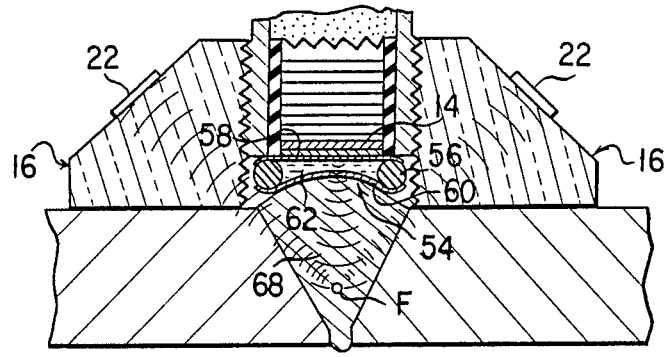
FIG. 11 is a diagrammatic illustration of parts of the FIG. 9 probe shown together with an object being tested, in order to explain its mode of operation.

In the use of the alternative probe 10a, as for inspecting a weld line 68 as in FIG. 11, the probe may be placed against the weld, and the transducer holder 50 may be revolved to urge the elastic coupling 54 against the weld. The lower elastic sheet 60 will readily undergo elastic deformation to conform to the surface shape of the weld 68. Also, as the elastic coupling 54 is pressed against the object, the oil or like fluid that has been injected in the fluid chamber 62 will seep out, filling the interstices between the lower elastic sheet 60 and the weld 68 to permit effective transmission of ultrasonic vibrations.

The ultrasonic vibrations emanating from the first transducer 14 will travel through the elastic coupling 54 into the weld 68. If a flaw F exists in the neighborhood of the point P explained in connection with the FIG. 1 embodiment, the reflections of the ultrasonic vibrations therefrom will be accurately captured by the pair of second ultrasonic transducers 22 which are both oriented as aforesaid toward the point P.

Difficulties heretofore encountered in the inspection of weld beads in particular are due to their irregular surface shapes which either block the passage of the transmitted waves or cause the preparation of the reflected waves in diffuse directions. We have eliminated these difficulties by providing the elastic coupling 54 which is capable of close contact with bead surfaces.

Another pronounced advantage of the elastic coupling 54 is that, when placed aginst the bead as in FIG. 11, the coupling is deformed into a concave acoustic lens which functions to converge and intensify the ultrasonic vibrations. The ultrasonic probe 10a is therefore sensitive to much smaller flaws than is the comparable prior art.

Figure 12:
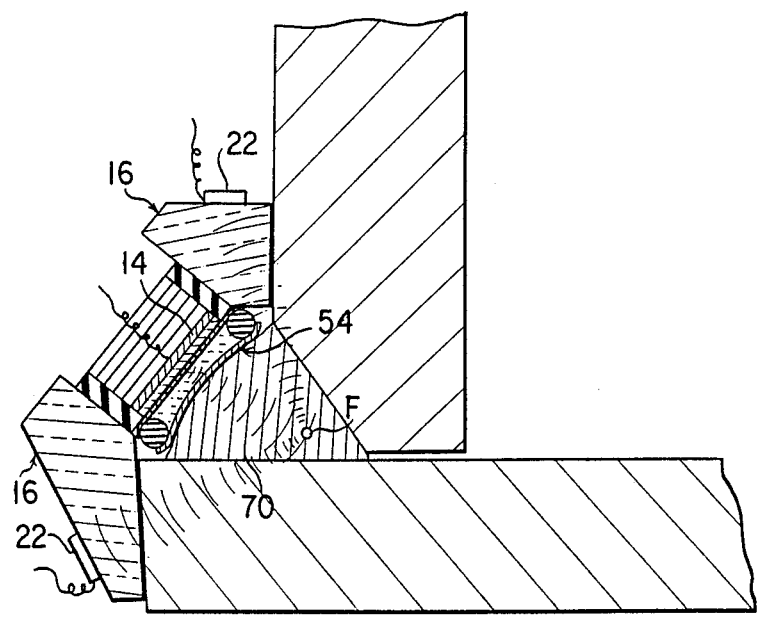
FIG. 12 is an illustration similar to FIG. 11 but showing a slight modification of the FIG. 9 probe.

The probe 10a is readily adaptable for the inspection of a fillet weld 70, as in FIG. 12, merely by correspondingly modifying the shape of the lenses 16.

We understand, of course, that various additional modifications may be made in the form, arrangements, proportions and other details of the illustrated examples of ultrasonic probes without departing from the scope of our invention.

We claim:

1. A probe for ultrasonic flaw detection comprising:
   (a) a housing having an open bottom and an axis passing therethrough;
   (b) a first ultrasonic transducer disposes at the open bottom of the housing and centerd about the axis thereof;
   (c) lens means disposed within the housing and exposed through the open bottom thereof, the lens means having at least one sloping surface at an angle to the axis of the housing;
   (d) at least one pair of second ultrasonic transducers mounted on the sloping surface of the lens so as to provide paths of ultrasonic vibrations extending through the lens means, the paths of ultrasonic vibrations crossing each other at that point on the axis of the housing which is located outside the open bottom thereof.

2. The probe of claim 1 further comprising means for acoustically insulating the first and the second ultrasonic transducers from each other.

3. The proble of claim 2 wherein the acoustically insulating means comprises:
   (a) first damper means between the first ultrasonic transducer and the lens means;
   (b) second damper means affixed to the second ultrasonic transducers; and
   (c) a mass of damping material filled in the housing.

4. The probe of claim 1 wherein the lens means comprises a pair of lenses disposed on the opposite sides of the first ultrasonic transducer and each having one sloping surface on which one second ultrasonic transducer is mounted.

5. The probe of claim 1 wherein the lens means comprises at least three lenses disposed around the first ultrasonic transducer and each having one sloping surface on which one second ultrasonic transducer is mounted.

6. The probe of claim 1 wherein the lens means comprises a lens substantially in the shape of a truncated cone centered about the axis of the housing and having the second ultrasonic transducers mounted thereon.

7. The probe of claim 1 wherein the lens means comprises a lens substantially in the shape of a stack of two truncated cones centered about the axis of the housing and each having one second ultrasonic transducer mounted thereon.

8. The probe of claim 1 further comprising means for adjustably moving the first ultrasonic transducer back and forth relative to the housing in the direction of the axis of the housing.

9. The probe of claim 8 wherein the adjustably moving means comprises a transducer holder of cylindrical shape centered about the axis of the housing and having the first ultrasonic transducer mounted thereto, the transducer holder being threadedly engaged with the lens means for movement with the first ultrasonic transducer along the axis of the housing relative to the lens means.

10. The probe of claim 1 further comprising a coupling underlying the first ultrasonic transducer and adapted for direct contact with an object to be inspected, the coupling being capable of elastic deformation to conform to the shape of the object.

11. The probe of claim 10 wherein the coupling comprises:
 (a) a ring;
 (b) a first sheet of elastic material attached to one side of the ring and having the first ultrasonic transducer mounted thereon; and
 (c) a second sheet of elastic material attached to another side of the ring and defining in combination with the first sheet a fluid chamber to be filled with a fluid, the second sheet being adapted to permit the fluid to seep out therethrough when the second sheet is held against an object to be inspected.

12. The probe of claim 11 wherein the first sheet of the coupling is thinner than the second sheet.

* * * * *